United States Patent [19]

Latimer et al.

[11] Patent Number: 5,154,185
[45] Date of Patent: Oct. 13, 1992

[54] AIR EVACUABLE SUPPORT

[75] Inventors: Elizabeth M. Latimer, Escondido; Hy H. Zornes, Fallbrook, both of Calif.

[73] Assignee: Hartwell Medical Corporation, Carlsbad, Calif.

[21] Appl. No.: 613,214

[22] Filed: Nov. 14, 1990

[51] Int. Cl.⁵ ............................................. A61F 5/37
[52] U.S. Cl. ..................................... 128/870; 602/6; 602/19; 128/DIG. 20
[58] Field of Search ......... 128/78, 845, 870, DIG. 20, 128/84 C, 85, 87 R, 87 B, 89 R, 89 A, 869

[56] References Cited

U.S. PATENT DOCUMENTS

| | | | |
|---|---|---|---|
| 2,489,828 | 11/1949 | Springer | 5/628 |
| 2,655,916 | 10/1953 | Timmins | 128/87 R |
| 2,766,751 | 10/1956 | Topa | 128/870 |
| 3,135,972 | 6/1964 | Jakes et al. | 5/627 |
| 3,158,875 | 12/1964 | Fletcher | 5/628 |
| 3,212,497 | 10/1965 | Dickinson | 602/6 |
| 3,232,289 | 2/1966 | Zimmerman | 128/87 R |
| 3,399,670 | 9/1968 | Veasey | 128/870 |
| 3,740,777 | 6/1973 | Dee | 128/845 X |
| 3,745,998 | 7/1973 | Rose | 602/6 |
| 3,762,404 | 10/1973 | Sakita | 602/6 |
| 3,814,088 | 6/1974 | Raymond | 128/87 R |
| 4,024,861 | 5/1977 | Vincent | 602/19 |
| 4,045,830 | 9/1977 | Loeb et al. | 5/81.1 |
| 4,127,120 | 11/1978 | Applegate | 128/870 |
| 4,141,368 | 2/1979 | Meyer | 128/870 X |
| 4,182,320 | 1/1980 | Sweeney | 128/89 R |
| 4,211,218 | 7/1980 | Kendrick | 128/870 X |
| 4,234,982 | 11/1980 | Bez et al. | 5/455 |
| 4,261,349 | 4/1981 | Lamsson et al. | 128/89 R |
| 4,301,791 | 11/1981 | Franco, III | 128/DIG. 20 |
| 4,428,087 | 1/1984 | Horn | 5/449 |
| 4,492,225 | 1/1985 | Picolet et al. | 602/5 |
| 4,580,555 | 4/1986 | Coppess | 602/23 |
| 4,657,003 | 4/1987 | Wirtz | 128/869 |
| 4,665,908 | 5/1987 | Calkin | 128/870 |
| 4,766,890 | 8/1988 | Hollrah | 602/14 |
| 4,862,879 | 9/1989 | Coombs | 128/DIG. 20 X |

FOREIGN PATENT DOCUMENTS

| | | | |
|---|---|---|---|
| 275320 | 7/1988 | European Pat. Off. | 128/87 R |
| 2602492 | 7/1976 | Fed. Rep. of Germany | 128/87 R |
| 1591024 | 6/1981 | Fed. Rep. of Germany | 128/845 |
| 2530946 | 2/1984 | France | 128/89 R |
| 160799 | of 1964 | U.S.S.R. | 128/87.2 |

OTHER PUBLICATIONS

Evac-U-Splint Publication.
Vocuum Splint Publication (Japanese).
Vacuum Fixer Publication (Japanese).

Primary Examiner—Robert A. Hafer
Assistant Examiner—Kevin G. Rooney
Attorney, Agent, or Firm—J. F. McLellan

[57] ABSTRACT

An air evacuable support comprising an elongated, airtight and flexible casing partially filled with a plurality of beads which are conformable to a person's body contours. The support can be formed into a seat configuration for placement upon a wheelchair or the like. Apertured baffles located within the casing slow the resulting downward movement of the beads, but also enable the beads to be forcibly moved through them by an attendant for proper bead concentration in areas needing greater rigidity or support. Such rigidity is developed upon evacuation of air from the casing. The seated person is cradled and closely supported by the compacted beads.

13 Claims, 3 Drawing Sheets

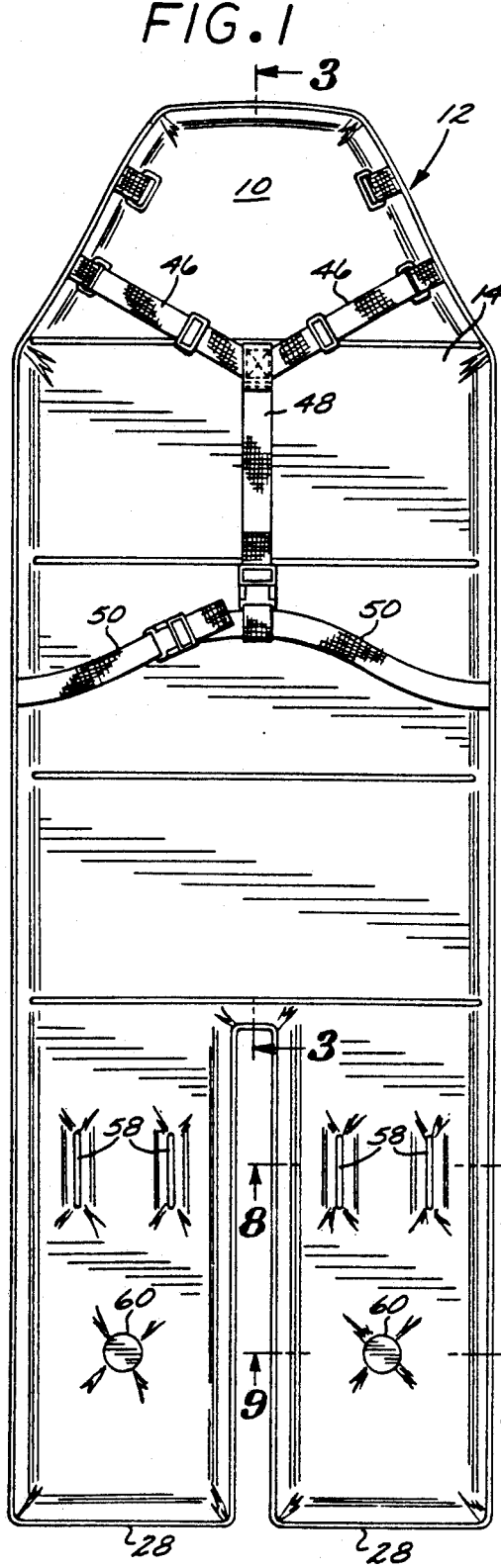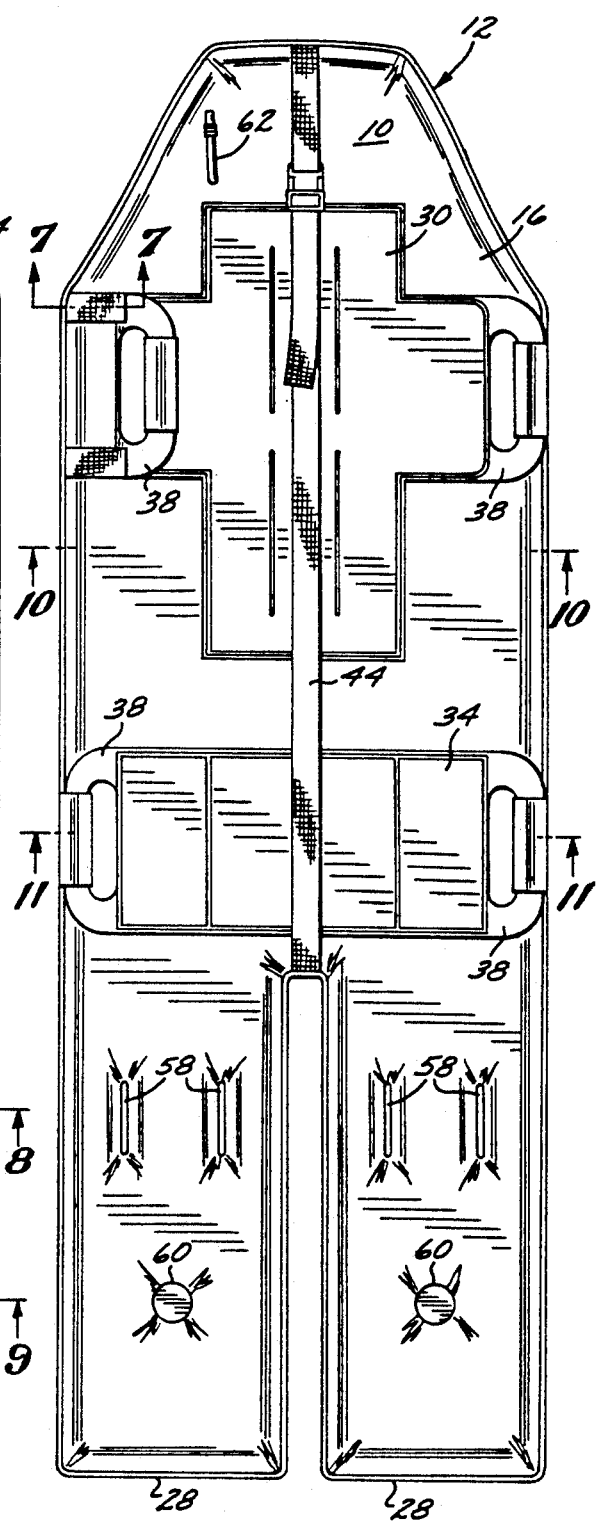

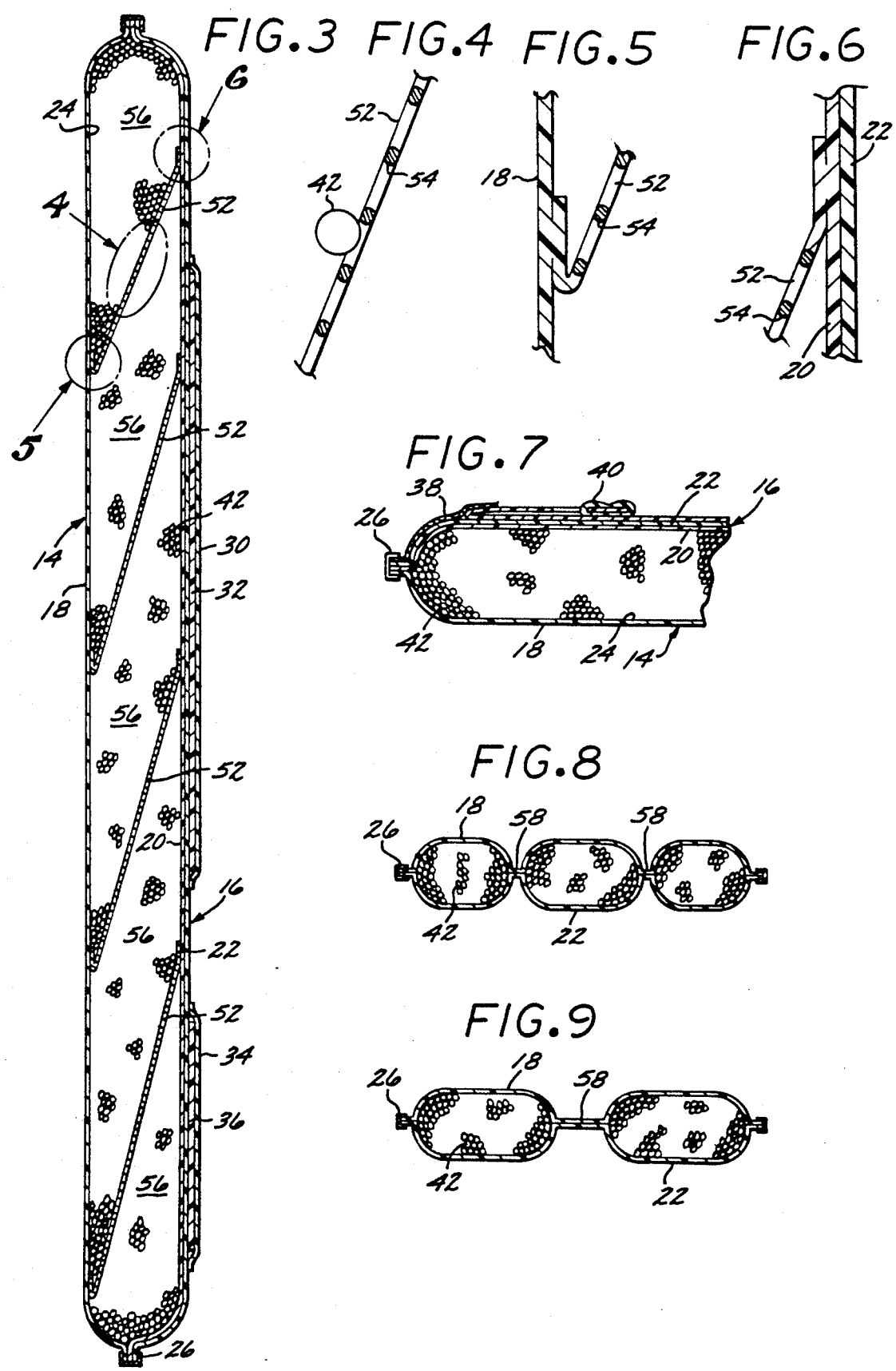

AIR EVACUABLE SUPPORT

CROSS REFERENCE TO RELATED APPLICATION

This application is related to co-pending patent application Ser. No. 07/556,733, filed Jul. 20, 1990, and having the same assignee as the present application.

BACKGROUND OF THE INVENTION

1. Field of the Invention

The present invention relates to an air evacuable support and particularly one adapted for non-horizontal use to support a person in a seated position.

2. Description of the Prior Art

Persons suffering physical impairment or disability by reason of advanced age, injuries, medical afflictions or the like are often not adequately supported by conventional household furniture, or by vehicle seats or wheel chairs. Such seating arrangements do not provide comfortable, conformable cushioning, nor do they provide sufficient immobilization against lateral movement or forward movement out of the seat. This is particularly true of persons whose bodies are disfigured or malformed. Adequate, comfortable support is especially important for victims of Marfan syndrome, a genetic disease which affects the connective tissues of the skeleton, lungs, eyes, heart and other organ systems such that the tissue does not adequately hold the body parts in position.

Specially formed cushions have heretofore been fabricated to conform to the precise body contours of an individual. This provides adequate support and prevents any movement that would aggravate existing medical afflictions or develop secondary trauma, but since such a support system has to be specially tailored to a particular individual it is too expensive for most persons.

One of the better immobilization means of the prior art is disclosed in the previously mentioned co-pending patent application Ser. No. 07/556,733, filed Jul. 20, 1990. The disclosed system comprises an air evacuable casing filled with small discrete elements such as round beads. The casing is normally horizontally oriented to support a person placed upon the casing, which extends up the sides of the person to cradle and support the body.

Once the beads are properly located or displaced to conform to the contours of the body, the casing is evacuated. This draws the beads together into a rigid mass. It has been found that such an arrangement comfortably supports and substantially immobilizes a person in a horizontal position so that the person can be safely transported without causing discomfort or secondary trauma.

However, it has also been found that when this type of immobilization device is oriented to rest upon a wheelchair the beads in the elevated portion of the casing tend to abruptly fall into the less elevated portions and are difficult to upwardly redistribute for molding about upper areas of the body where support is needed. It would appear that isolating the beads by using partitions to form separate compartments in the casing might solve the problem, but this has not proven to be satisfactory. The skeletal structure of each individual, whether normal or malformed, is sufficiently unique that some degree of bead migration out of such local or separate compartments is necessary. For example, if an unusually high concentration of beads is needed in the shoulder area for proper support, beads cannot be moved out of their respective compartments to supply this need.

Thus, there is an unmet need for an air evacuable support which can be used with wheelchairs, vehicle seats, airline seats, or with conventional household chairs and sofas. A suitable support must adequately cushion and support the body through proper bead distribution despite the orientation of the support in a seat configuration.

SUMMARY OF THE INVENTION

According to the present invention, an air evacuable support is provided which is adapted not only to support a person comfortably in a seated position, but also to substantially immobilize the person against any movement that might result in secondary trauma.

The support is portable and can be quickly and easily placed in position upon any of a variety of seating devices, including a vehicle seat, a wheelchair, an aircraft seat, a propped up bed, living room furniture, etc.

The support comprises an elongated casing having front and back wall means which define an interior containing a plurality of discrete elements such as beads. When a person is placed upon the casing a certain amount of conformation of the beads to the contours of the body occurs simply by migration or movement of the beads because of the person's weight. Further movement or molding of the beads to support areas needing higher bead concentrations for greater rigidity can be done by an attendant or orderly. Following this, evacuation of the casing interior urges the beads together into a rigid mass having the shape previously imparted to the loose beads before the casing was evacuated.

It is a feature of the present invention that the support includes a plurality of bead migration control means or baffles which extend between the casing front and back walls at longitudinally spaced intervals. This enables initial retention of masses or groups of beads within separate support regions. However, each baffle is apertured so that elevation of one region relative to an adjacent region causes a regulated flow or passage of the beads through the intervening baffle. The rate of passage is sufficiently slow that there is ample time for an attendant to manually move or mold the beads where necessary before the beads fall out of position of their own weight. The configuration and orientation of the baffles is not only effective to slow bead passage downwardly under the force of gravity, but beads are relatively easily forced through the baffles by an attendant during the molding procedure. One arrangement which permits this is a sloping or diagonal arrangement of the baffles relative to the casing front and back walls.

The sloped baffles allow the beads to fall downwardly under the force of gravity, but their rate of descent or downward migration is slowed because the beads can only pass through the baffles if they follow transverse paths through the baffle apertures. However, an attendant can easily impart such transverse bead travel by pressing against the beads while molding them.

The present support is also preferably characterized by stiffeners to support the person's back, especially during the period prior to casing evacuation. Also, the support preferably includes separate leg portions so that each leg can be elevated separately of the other. The leg portions preferably also include special baffles to slow downward bead migration.

In a preferred embodiment the support includes straps for attaching it to structure of the seat upon which it is placed. Additional straps are provided to hold the user and constrain him or her from pitching forwardly out of the support.

The present support thus comprises a form of air evacuable "mattress" which cradles and supports a person by using beads to eliminate pressure points. The beads make specially formed padding unnecessary. They also provide insulation against escape of body heat, and they can easily be distributed during elevation of portions of the casing for conformity to a person's body. It is particularly effective for transporting seated patients having accident related injuries or disease-caused infirmities like the connective tissue deterioration associated with Marfan syndrome.

Other aspects and advantages of the present invention will become apparent from the following more detailed description taken in conjunction with the accompanying drawings.

BRIEF DESCRIPTION OF THE DRAWINGS

FIG. 1 is a top plan view of the air evacuable support according to the present invention;

FIG. 2 is a bottom plan view of the support of FIG. 1;

FIG. 3 is an enlarged view taken along the line 3—3 of FIG. 1;

FIG. 4 is an enlarged view taken in the area designated by the numeral 4 in FIG. 3;

FIG. 5 is an enlarged detail view taken in the area designated by the numeral 5 in FIG. 3;

FIG. 6 is an enlarged detail view taken in the area designated by the numeral 6 in FIG. 3;

FIG. 7 is an enlarged view taken along the line 7—7 of FIG. 2;

FIG. 8 is an enlarged view taken along the line 8—8 of FIG. 1;

FIG. 9 is an enlarged view taken along the line 9—9 of FIG. 1;

DESCRIPTION OF THE PREFERRED EMBODIMENT

Figure 10:
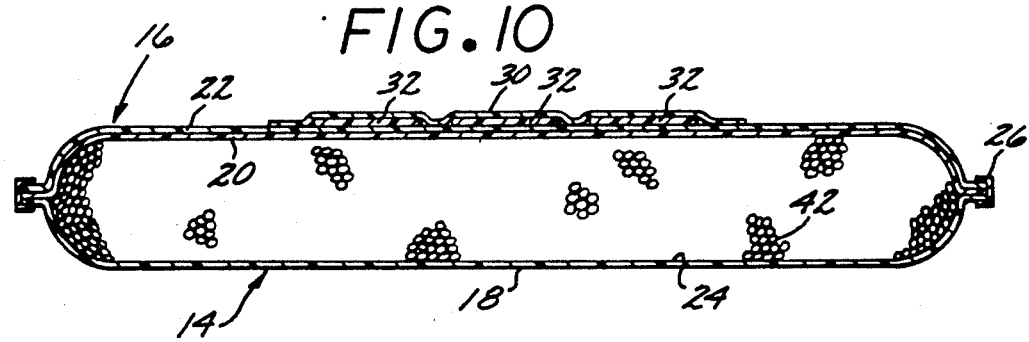
FIG. 10 is an enlarged view taken along the line 10—10 of FIG. 2.

Referring now to the drawings, and particularly to FIGS. 1-3, the present air evacuable support 10 comprises, generally, an elongated airtight and flexible bag or casing 12 upon which a person can be placed. The casing is formed of complemental front and back walls 14 and 16. As best seen in FIG. 3, the front wall 14 is comprised of a single sheet 18 while the back wall 16 comprises an intermediate sheet 20 and a back sheet 22. All of the sheets are similarly configured except that the intermediate sheet 20 only extends from the upper extremity to just below the mid portion of the casing. The sheets are sealed together at their edge margins by heat sealing or the like to define an airtight interior 24.

A reinforcing strip 26 made of the same material as the sheets 18, 20 and 22 is disposed about the edge margins of the sheets and is stitched in place to strengthen the heat sealed joint.

The casing 12 is generally elongated and substantially rectangular, tapering inwardly somewhat at the head extremity, while at the opposite extremity the casing is configured to include a pair of leg portions 28.

The sheets 18, 20 and 22 can be made of any suitable flexible material, fabric reinforced or otherwise, having adequate gas impermeability and wear characteristics. A woven nylon material with a protective coating such as urethane has been found to be satisfactory. This material provides a smooth surface for easy cleaning, and it is resistent to attack by chemical mixtures. The intermediate sheet 20 need not be gas impermeable and need not have the wear characteristics of the front and back sheets 18 and 22. As will be seen, the intermediate sheet 20 is provided for convenience of fabrication of the casing and in certain embodiments it would be possible to eliminate the intermediate sheet 20 altogether.

An upper stiffener section 30 made of the same kind of plastic material as the sheets 18, 20 and 22 is heat sealed at its edge margins to the back sheet 22. It is also heat sealed in its central portion to define three transversely spaced, longitudinally extending pockets which receive, respectively, three stiffeners or battens 32, as best seen in FIG. 10.

The buttocks or seat portion of the casing includes a stiffener section 34 made of plastic material similar to the section 30. It is also heat sealed at its edge margins to the casing back sheet 22. It is further heat sealed along transversely spaced, longitudinally extending areas to define a central slot or pocket which receives a stiffener panel 36, as best seen in FIG. 11.

Figure 11:
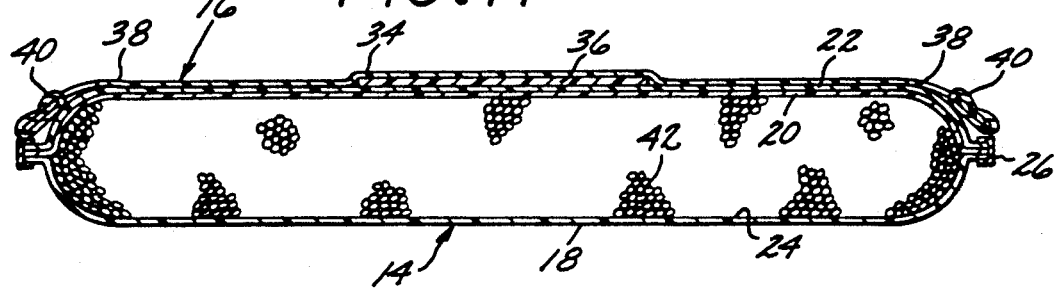
FIG. 11 is an enlarged view taken along the line 11—11 of FIG. 2.

Referring now to FIGS. 2, 7 and 11, handle sections 38 made of sheet plastic material like that of the casing sheets are provided with hand openings. The sections 38 are heat sealed to the opposite side extremities of the stiffener sections 30 and 34 to provide four handles 40, as best seen in FIG. 2.

The casing interior 24 is partially filled with a plurality of any suitable discrete elements or beads 42 operative upon evacuation of the casing to become a rigid, solid mass, as is well known in the art. These beads can be made of expanded or solid plastic material, such as polystyrene or polyvinylchloride or, if desired, they can be made hollow and therefore be compressible to reduce the formation of large wrinkles in the casing upon evacuation.

The loose beads 42 and flexible casing permit the casing side edges to be formed up against the sides of the person being supported to cradle and support the person on the casing. During this positioning of the casing the beads 42 are urged into conformity with the person's body by an attendant or orderly. Typically the beads are concentrated in those regions where greater support or rigidity is required.

As best seen in FIG. 2, a longitudinally oriented strap 44 is suitably mounted to the exterior of the back sheet 22. It extends over the head end of the casing and through the space between the leg portions 28. This strap is designed to be disposed over the top and underneath the seat of a wheelchair, vehicle, etc., (not shown) to secure the support 10 in place. In addition, a strap arrangement is provided to hold a person in position upon the support itself. The arrangement includes straps 46 whose outer ends are suitably secured to opposite edge portions of the upper extremity of the casing. They are joined at their inner ends to the upper end of a vertically or longitudinally oriented strap 48 which is located to overlie the chest of the person being supported.

The lower end of strap 48 is adapted for detachable connection by suitable strap fittings to the inner ends of a pair of straps 50. The outer ends of the straps 50 are suitably attached to opposite edges of the casing in the middle or waist region of casing, as best seen in FIG. 13.

Any arrangement of straps can be used which are effective to support a person in position upon the casing, the particular straps disclosed merely being exemplary. This is also true of the particular battens and the batten locations illustrated. Use of the battens 32 is preferred to provide resistance to transverse bending of the upper portion of the casing in its unevacuated state. Use of the stiffener panel 26 is also preferred because of the buttocks support it provides in the seat region. However, if desired, other forms of stiffening means may be utilized, or the stiffening means may be omitted altogether.

It is a particular feature of the present support 10 that means are provided for dividing or compartmentalizing the casing into longitudinally spaced regions which each contain a mass of the beads 42, with bead migration control means being provided to control the rate of flow between such regions.

Figure 13:
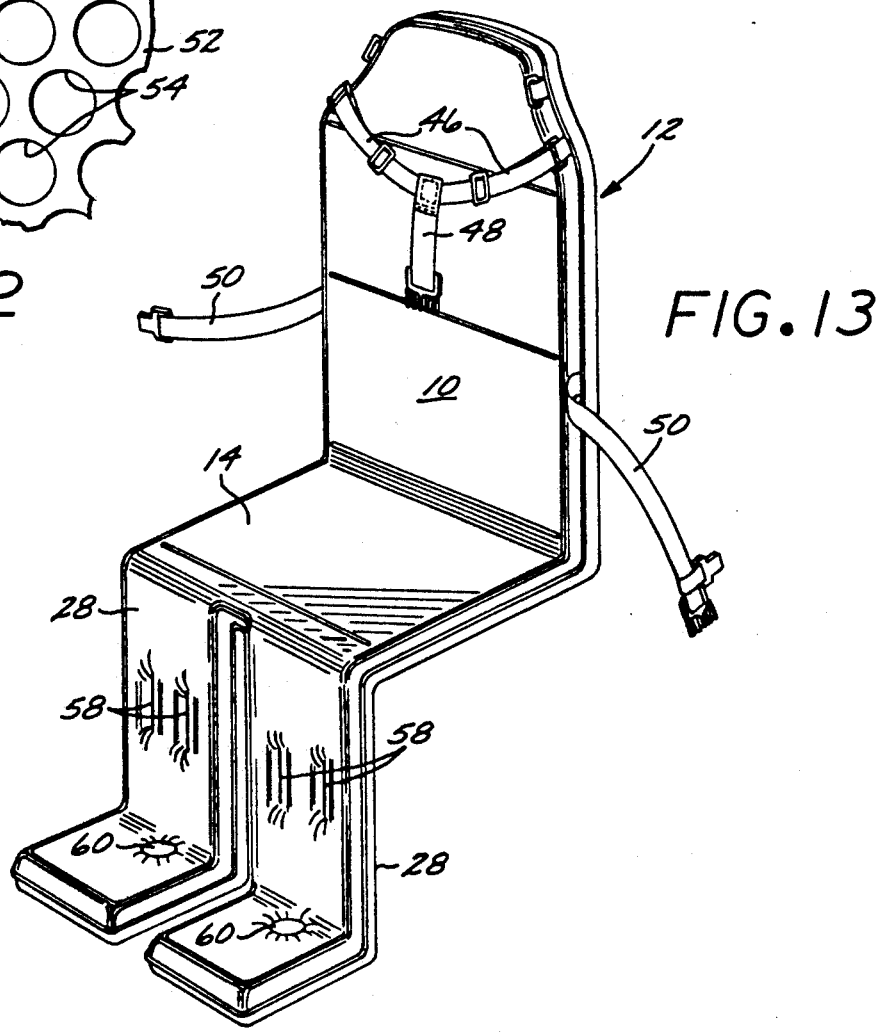
FIG. 13 is a perspective view of the present support as it would be oriented for use on a wheelchair (not shown), for example.

More particularly, the support 10 can be formed into the configuration illustrated in FIG. 13 to enable it to be placed upon a seat structure such as a wheelchair (not shown). In this position the beads 42 normally would abruptly dump or fall into the lower portions of the casing. This would make it very difficult for an attendant to reorient the beads to upper casing regions where they are also needed to provide adequate support.

As best seen in FIG. 3, a plurality of control means are provided to regulate migration or movement of the beads 42. In the embodiment illustrated the control means takes the form of a plurality of baffles 52.

Figure 12:
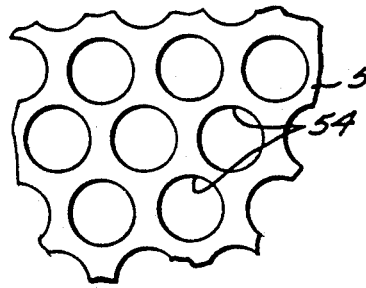
FIG. 12 is an enlarged plan view of one of the apertured baffles.

The baffles 52 preferably include a plurality of round openings or apertures 54, as best seen in FIG. 12. The apertures 54 are dimensioned to pass the round beads 42, the relative size of the beads 42 and apertures 54 being readily determinable by one skilled in the art to provide the results which will subsequently be described.

The baffles 52 can be made of sheet material punched out to provide the apertures, or a suitable fabric can be utilized which is woven to integrally include the desired apertures.

Each baffle 52 is generally rectangular and extends transversely across the casing interior 24. The baffles are longitudinally spaced apart to define longitudinally separated regions 56 located in the upper portion of the casing above the leg portions 28, as seen in FIGS. 1 and 3.

The baffles are preferably inclined or arranged diagonally relative to the front and back walls 14 and 16, with their lower edges suitably secured by heat sealing or the like to the inner surface of the front sheet 18, as seen in FIG. 5. The opposite or upper edges of the baffles are similarly secured to the inner surface of the intermediate sheet 20, as best seen in FIG. 6. The upper baffle edges could have been sealed to the back sheet 22 except for the presence of the stiffener sections 30 and 34. Therefore, the extra or intermediate sheet 20 is used to provide a sheet to which the upper baffle edges could readily be attached.

The rate of flow of the beads through the baffles 52 in the support orientation illustrated in FIG. 13 is slowed because the beads must travel along substantially transverse paths. This is seen in the detail showing of FIG. 4. Such transverse travel is not aided by gravity. The resulting slower migration of the beads enables a person to be placed upon the casing, with ample time for the beads to be sculpted or packed around the person conformably to his or her body contour, and for the casing to be evacuated. However, the beads can be easily manually moved or manipulated transversely through the baffles by an attendant to locate the beads in regions where they are needed.

The beads 42 in the leg portions 28 of the casing are also regulated in their downward passage. This is done by longitudinally extending heat seals 58 which adhere the front and back sheets 18 and 22 together, as best seen in FIG. 8. Generally circular heat seals 60 are also provided in the lower extremities or feet of the leg portions 28. These adhere together the front and back sheets 18 and 22 to define bead free solid areas for the heels of the person on the support 10.

In use, the support 10 is placed upon the seat being used, such as a wheelchair for example, and it assumes the configuration illustrated in FIG. 13. The strap 44 is then disposed around the wheelchair seat and back (not shown) to secure the support in position.

The person to be transported in the wheelchair is next placed upon the support 10 and an attendant then manually moves the beads 42 into conformity with the person's body. During this period downward travel of the beads 42 of their own weight is greatly slowed by the regulating effect of the baffles 52. The straps 46, 48 and 50 are then attached to bring the sides of the casing into closer engagement with the person's sides. Finally, a pump (not shown) is attached to a valve stem 62 of a suitable evacuation valve means located in the top of the casing, as seen in FIG. 2. Air is evacuated from the casing interior to rigidify the casing in close conformity with the person's body. In this rigid state a person can be transported in comfort without danger of any movement sufficient to cause secondary trauma.

From the foregoing it will be apparent that the present air evacuable support is uniquely adapted to cradle and support a patient in a substantially immobilized state, and in a seated position. Such a support is thus capable of use for transporting emergency or paramedic patients, for transporting patients in-hospital, and also for use in association with airline seats, elevatable beds, and conventional household chairs and couches, etc. The support eliminates pressure points, and thermally insulates a patient against loss of body heat. The firmness of support is easily varied by adjusting the degree of air evacuation from the casing.

Various other modifications and changes may be made with regard to the foregoing detailed description without departing from the spirit of the invention.

What is claimed is:

1. An air evacuable support comprising:
an elongated, airtight and flexible casing having internal front, back and opposite side walls defining a longitudinally extending interior, the casing being adapted for supporting a person in a horizontal position, the casing further having an extremity pivotable about a transverse axis from a horizontal orientation toward a generally upright orientation for supporting a person in a seated position;

air evacuation means for developing a vacuum in the interior;

a plurality of discrete elements in the casing interior movable in the unevacuated state of the casing to allow movement of the casing into conformity with the contours of the person and pivoting of the casing extremity toward the upright orientation, the discrete elements being immovable in the evacuated state of the casing to fix the casing in such conformity and in any selected orientation of the casing extremity; and a plurality of element migration control means attached to the front and back walls at longitudinally spaced intervals and of sufficient width to extend between the side walls to define longitudinally spaced apart support regions for the discrete elements, each control means being operative to allow generally longitudinal, gravity induced passage of discrete elements past it from the more elevated support regions to the less elevated support regions upon pivoting of the casing extremity toward the upright orientation, each control means being configured to enable such passage across its full width to establish a relatively even distribution of discrete elements across its width.

2. An air evacuable support according to claim 1 wherein each control means comprises an apertured baffle through which the discrete elements can pass.

3. An air evacuable support according to claim 2 wherein each baffle is made of fabric material arranged diagonally relative to the front and back walls whereby the path of passage of the discrete elements through the baffle is altered to slow such passage.

4. An air evacuable support according to claim 1 wherein the casing includes a pair of leg portions; and further comprising transversely spaced, longitudinally extending element migration control means in the leg portions defining transverse support regions and narrow paths therebetween to enable downward migration of discrete elements.

5. An air evacuable support according to claim 4 wherein the additional element migration control means comprises areas of attachment together of the front and back walls which define narrowed paths for downward bead migration.

6. An air evacuable support comprising:

an elongated, airtight and flexible casing having internal walls defining a longitudinally extending interior, the casing being adapted for supporting a person in a horizontal position, the casing further having an extremity pivotable about a transverse axis from a horizontal orientation toward a generally upright orientation for supporting a person in a seated position;

air evacuation means for developing a vacuum in the interior;

a plurality of generally spherical beads in the casing interior movable in the unevacuated state of the casing to allow movement of the casing into conformity with the contours of the person and pivoting of the casing extremity toward the upright orientation, the beads being immovable in the evacuated state of the casing to fix the casing in such conformity and in any selected orientation of the casing extremity; and a plurality of baffles attached to the interior walls of the casing and extending across the casing interior at longitudinally spaced intervals to define longitudinally spaced apart support regions for the beads, each baffle including a pattern of circular apertures across its width to allow generally longitudinal, gravity induced passage of beads from the more elevated support regions to the less elevated support regions upon pivoting of the casing extremity toward the upright orientation, the pattern of apertures enabling the passage of beads across the full width of the baffles to prevent a disproportionate collection of beads at any point along the width of the baffles.

7. An air evacuable support according to claim 6 wherein each baffle is arranged diagonally across the interior whereby the rate of flow of the beads through the baffle between adjacent support regions is slowed.

8. An air evacuable support according to claim 6 wherein the casing includes a pair of leg portions, and including bead migration control means in the leg portions.

9. An air evacuable support according to claim 8 wherein the bead migration control means comprises areas of attachment together of the casing walls which form the interior, the areas of attachment defining narrowed paths for downward bead migration.

10. An air evacuable support according to claim 1 wherein the casing extremity includes a plurality of transversely spaced, longitudinally extending pockets, and including a plurality of battens located in the pockets whereby in the relatively flexible state of the casing the casing extremity is constrained against bending.

11. An air evacuable support according to claim 1 wherein the casing includes longitudinally oriented strap means adapted to pass around the seat and back portions of a seating device for securing the support to the seating device.

12. An air evacuable support according to claim 1 wherein the casing includes strap means coupled to and adapted to extend across the casing for urging the sides of the casing against a person on the casing to cradle and support the person.

13. An air evacuable support according to claim 1 including pairs of carrying handles located on opposite sides of the casing.

* * * * *